(12) United States Patent
Hausheer

(10) Patent No.: US 7,235,589 B2
(45) Date of Patent: *Jun. 26, 2007

(54) METHOD OF TREATING PATIENTS UNDERGOING KIDNEY DIALYSIS

(75) Inventor: Frederick H. Hausheer, Fair Oaks Ranch, TX (US)

(73) Assignee: Bio Numerik Pharmaceuticals, Inc., San Antonio, TX (US)

( * ) Notice: Subject to any disclaimer, the term of this patent is extended or adjusted under 35 U.S.C. 154(b) by 81 days.

This patent is subject to a terminal disclaimer.

(21) Appl. No.: 10/945,810

(22) Filed: Sep. 21, 2004

(65) Prior Publication Data

US 2006/0063744 A1    Mar. 23, 2006

(51) Int. Cl.
*A61K 31/10*    (2006.01)

(52) U.S. Cl. ..................................... 514/711
(58) Field of Classification Search ............... None
See application file for complete search history.

(56) References Cited

U.S. PATENT DOCUMENTS

| | | | | |
|---|---|---|---|---|
| 5,302,609 | A | * | 4/1994 | Shayman et al. ........... 514/380 |
| 5,661,188 | A | * | 8/1997 | Weissman et al. .......... 514/711 |
| 6,031,006 | A | * | 2/2000 | Hausheer et al. ........... 514/711 |
| 6,172,119 | B1 | * | 1/2001 | Hausheer .................... 514/707 |
| 6,537,976 | B1 | * | 3/2003 | Gupta .......................... 514/52 |
| 2003/0040507 | A1 | * | 2/2003 | Nickel et al. ............... 514/110 |
| 2004/0096845 | A1 | * | 5/2004 | Sakai et al. .................... 435/6 |

OTHER PUBLICATIONS

The Merck Manual of Diagnosis and Therapy, 14th Edition, published 1982 by Merck Sharp & Dohme Research Laboratories, pp. 1510-1515.*

The Merck Manual of Diagnosis and Therapy, 14$^{th}$ Edition, published 1982 by Merck Sharp & Dohme Research Laboratories, (NJ), pp. 1518-1527.*

* cited by examiner

*Primary Examiner*—Raymond J. Henley, III
(74) *Attorney, Agent, or Firm*—Thomas J. Dodd; Scott A. Whitaker

(57) ABSTRACT

This invention relates to a method of treating patients who are receiving dialysis treatments. The method includes administering to a patient in need of treatment an effective amount of a thiol or reducible disulfide compound according to the formula set forth in the specification.

3 Claims, No Drawings

METHOD OF TREATING PATIENTS UNDERGOING KIDNEY DIALYSIS

FIELD OF THE INVENTION

This invention relates to a method for treating patients undergoing hemodialysis, commonly referred to as kidney dialysis. The method involves administering an effective amount of a disulfide or thiol-containing compound to the patient prior to undergoing the dialysis procedure.

BACKGROUND OF THE INVENTION

Hemodialysis, hereinafter referred to as kidney dialysis, or simply "dialysis, is a medical procedure that is performed on human patients (and also on a smaller scale, pet animals), to remove toxins from the blood in a similar manner to a functioning kidney. When a person or animal's kidneys cease to function properly due to one or more of a number of acute or chronic diseases or conditions (diabetes is a known causative factor in renal failure), toxins accumulate in the bloodstream.

Failure to remove these toxic compounds—primarily urea, uric acid and its analogues, and other nitrogenous compounds such as creatinine; and excess amounts of elements such as potassium, phosphorous, sodium, chloride and other minerals—from the blood results in deterioration of body tissues and organ systems, eventually resulting in death.

Dialysis may be performed in a hospital setting or clinic; or in some cases, the patient is trained to perform the procedure at home on an outpatient basis. Two primary types of dialysis are regularly performed—conventional hemodialysis and peritoneal dialysis. In conventional dialysis, the patient is connected (via an arteriovenous fistula, graft or by catheter) to a dialysis machine. The dialysis machine functions to pump the contaminated blood from the patient through a dialyzer, where the blood is filtered through a dialyzing solution, and thence returned to the patient. Conventional hemodialysis usually takes between 3-6 hours and is normally performed at a clinic or hospital several times per week.

In peritoneal dialysis, a catheter is inserted into the patient's abdomen, with the catheter connected its other end to a supply of dialysis solution. In a typical peritoneal dialysis exchange, dialysis solution is introduced into the patient's abdominal cavity through the catheter and allowed to remain there for a predetermined time period (called a "dwell"). During the period when the peritoneal cavity is filled with the solution, waste products and excess body fluids pass through the peritoneum, where they encounter the dialysis solution and are removed from the body when the solution is later drained from the body. The draining/filling process (the "cycle") is normally repeated several times daily, with a long dwell overnight. Periodic testing is performed to determine the efficacy of the dialysis.

Typical dialysis solution is a dextrose-based solution, with the solution also including a quantity of salt and other dissolved minerals, and perhaps electrolytes as determined by the needs of each patient. The dialysis solution functions to increase osmotic pressure in the peritoneal cavity to cause maximum diffusion of excess fluids and waste products from the blood. The dialysis solution also serves to bind waste products for removal during the draining process, and to deliver necessary minerals and electrolytes to the body (many renal failure patients are placed on diets that shortchange necessary minerals, and must be ingested separately).

Mesna (sodium 2-mercaptoethene sulfonate) and dimesna (disodium 2,2'-dithiobis ethane sulfonate) are known therapeutic compounds that have heretofore demonstrated a wide variety of therapeutic uses. Both mesna and dimesna have been shown to be effective protective agents against certain specific types of toxicity associated with the administration of cytotoxic drugs used to treat patients for various types of cancer.

In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

The near absence of toxicity of dimesna further underscores the usefulness of this compound, as large doses can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The molecular structures of both mesna and dimesna are shown below as Structure I and Structure II respectively.

$$HS-CH_2-CH_2-SO_3Na \qquad (I)$$

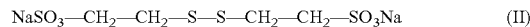

$$NaSO_3-CH_2-CH_2-S-S-CH_2-CH_2-SO_3Na \qquad (II)$$

As shown, dimesna is a dimer of mesna, with the optimum conditions for oxidation occurring in the slightly basic (pH ~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with certain platinum agents and/or taxanes.

Dimesna, as well as some analogues, have excellent toxicity profiles in mammalian species. In fact, dimesna has been administered intravenously to mice and dogs in doses higher than the accepted oral $LD_{50}$ for common table salt (3750 mg/kg), with no adverse effects. Dimesna has also been administered to humans in doses exceeding 40 $g/m^2$, with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration, usually a hydroxy, aquo or superoxide is located. Mesna also tends to form conjugates with naturally occurring biochemicals that contain a free thiol moiety, such as cysteine, glutathione, homocysteine, and others.

Dimesna and other disulfides can be activated intracellularly by glutathione reductase, a ubiquitous enzyme, thereby generating high concentrations of intracellular free thiols.

These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well known in the art. One such method involves the two-step, single pot synthetic process for making dimesna and like compounds of the following formula:

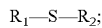

wherein:
$R_1$ is hydrogen, X-lower alkyl, or X-lower alkyl-$R_3$;
$R_2$ is -lower alkyl-$R_4$;
$R_3$ and $R_4$ are each individually $SO_3M$ or $PO_3M_2$;
X is absent or X is sulfur; and
M is an alkali metal.

The process essentially involves a two-step single pot synthetic process, which results in the conversion of an alkenyl sulfonate salt or acid to the desired formula I compound. The process in the case of mesna is a single step process that converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well known and documented in the prior art, may be employed to make either mesna or dimesna, or derivatives and analogues thereof.

SUMMARY OF THE INVENTION

This invention involves the administration of an effective amount of a compound of formula I, below, to a patient undergoing or about to undergo dialysis.

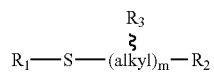

(I)

wherein:
$R_1$ is hydrogen, lower alkyl or

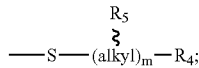

$R_2$ and $R_4$ are each individually $SO_3^-M^+$, $PO_3^{2-}M_2^{2+}$, or $PO_2S^{2-}M_2^{2+}$;
$R_3$ and $R_5$ are each individually hydrogen, hydroxy or sulfhydryl;
Each m is individually 1, 2, 3, 4, 5 or 6 with the proviso that if m is 1, then $R_3$ is hydrogen; and
M is hydrogen or an alkali metal ion; or
a pharmaceutically acceptable salt thereof.

Effective amounts of the formula I compound to be administered according to the method of this invention are variable, and depend upon the individual patient's needs and on the patient's response. The effective amount will also vary based upon the type of formula I compound to be administered, with disulfides usually requiring higher doses than thiols for effective treatment. Also, the type of dialysis procedure will affect the effective amount of administered formula I compound.

However, due to the excellent toxicity profile of the formula I compounds, large amounts of the agent may be administered, such as by continuous IV drip or multiple oral doses, without risk of untoward side effects commonly associated with other drugs used to treat this condition.

Accordingly, it is an object of this invention to provide for a method of safely and effectively enhancing the efficacy of dialysis treatments.

Another object is to provide a method of enhancing performance of a dialysis procedure by administration of a thiol or reducible disulfide to the patient undergoing or about to undergo dialysis treatment.

Other objects will become apparent upon a reading of the following description.

DESCRIPTION OF THE PREFERRED EMBODIMENTS

The preferred embodiments herein described are not intended to be exhaustive or to limit the invention to the precise form disclosed. They are chosen and described to explain the principles of the invention, and its application and practical use to best enable others skilled in the art to follow its teachings.

The method of this invention involves the administration of an effective amount of a formula I compound to a patient undergoing or about to undergo kidney dialysis treatment. The effective amount of the formula I compound will necessarily depend upon the individual patient's response. Since the formula I compounds are essentially nontoxic and cleared rapidly from the patient's body, large amounts of the formula I compound can normally be safely administered.

One preferred method of this invention involves adding an effective amount of the formula I compound to the bag containing dialysis solution that is employed in peritoneal dialysis. Typical dialysis bags are between 1.5 L-3.0 L, and the effective amount of formula I compound ranges from as low as 15 mg (10 mg/L to 20 mg/L) to as high as 200 g (~25 mg/mL to ~200 mg/mL) of formula I compound.

The preferred formula I compounds are disulfides; larger amounts of these preferred compounds may be given safely and effectively when compared to corresponding thiols and thioethers. The most preferred compound is disodium 2,2'- dithiobis ethane sulfonate (dimesna or Tavocept™) administered at a dose of between 10 g to 100 g added to the dialysis bag.

Another preferred embodiment of this invention is to administer the formula I compound to a patient prior to beginning a hemodialysis treatment. The formula I compound is normally administered at a predetermined time prior to beginning of dialysis, preferably 5 minutes to 1 hour prior to the commencement of treatment, most preferably 15 to 30 minutes prior to commencement.

Alternatively, the formula I compound may be added to the dialysis solution contained in the dialysis machine. As previously stated, the most preferred compounds of formula I are the disulfides, and effective amounts of these compounds to be administered to the patient range from 15 mg to 80 g. Most preferred are disulfides with dosages that range from 1 g-40 g. When the formula I compound is added to the dialysis solution, the effective amount is defined as a concentration of the formula I compound ranging between 0.1 mg/mL to 200 mg/mL of solution.

For parenteral administration to the patient, the formula I compound is dissolved in a suitable solvent, most preferably water, to produce a solution. One or more pharmaceutically acceptable excipients may also be added to provide for an elegant formulation. The resulting formulation may then be administered by intravenous push or by drip infusion or other accepted medical procedure.

For oral administration the formula I compound is preferably combined with one or more pharmaceutically acceptable excipients, fillers and/or diluents. Oral dosage forms may include pills, caplets, tablets, and others. Alternatively, the formula I compound may be contained in a deglutable container such as a gelatin capsule or the like, or may be dissolved in water for the patient to drink prior to commencement of dialysis. Additional doses of the formula I compound may be repeated if the dialysis treatment lasts more than a few hours.

Careful monitoring and analysis is performed regularly during hemodialysis, with additional doses administered as needed. During peritoneal dialysis, most often performed at home by the patient and an assistant, monitoring may be performed as well to assess the effectiveness of the dialysis, and adjustments made in the treatment as necessary.

The following hypothetical example is offered to explain the working aspects of the invention.

EXAMPLE 1

Continuous Ambulatory Peritoneal Dialysis (CAPD)

The patient about to undergo CAPD is fitted with an abdominal catheter. The open end of the catheter is connected to a 2 L bag of dialysis solution, which contains the following dissolved constituents: 100 g of dextrose; 10 g of sodium chloride; 5 g of sodium lactate; 2 g of calcium chloride; 1 g of magnesium chloride; and 40 g of dimesna.

The dialysis solution flows from the bag into the patient's abdomen and the bag is disconnected. The solution is allowed to "dwell" in the patient's abdomen for between 4 to 6 hours, then the catheter is reconnected to the bag and the solution is drained from the abdomen back into the bag. The process is repeated 2 to 4 times daily, and again just prior to the patient's going to sleep at night, whereupon the solution dwells in the abdomen for 6 to 8 hours. Spent dialysis solution may be analyzed from time-to-time in order to determine the efficiency of the dialysis, and to make modifications in treatment, if necessary.

It is understood that the above description is in no way limiting of the invention, which may be modified within the scope of the following claims.

What is claimed is:

1. A method of enhancing the therapeutic detoxification process of kidney dialysis in a mammalian patient by reducing the concentrations of free radicals and other nucleophilic compounds which cause cellular damage, said method comprising administering to the patient a dialysis solution which contains as a component an effective amount of formula I compound comprising:

(I)

wherein:
  $R_1$ is hydrogen, lower alkyl or

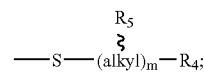

$R_2$ and $R_4$ are each individually $SO_3^-M^+$, $PO_3^{2-}M_2^{2+}$, or $PO_2S^{2-}M_2^{2+}$;
  $R_3$ and $R_5$ are each individually hydrogen, hydroxy or sulfhydryl;
  Each m is individually 1, 2, 3, 4, 5 or 6 with the proviso that if m is 1, then $R_3$ is hydrogen; and
  M is hydrogen or an alkali metal ion; or
  a pharmaceutically acceptable salt thereof.

2. The method of claim 1 wherein the formula I compound is dimesna and the concentration of dimesna administered to the patient as a component of the dialysis solution is from approximately 0.1 mg/ml to approximately 250 mg/ml.

3. The method of claim 1 wherein the formula I compound is dimesna and the total effective amount of dimesna received by the patient as a component of the dialysis solution is from approximately 1 g/m² to approximately 80 g/m².

* * * * *